(12) United States Patent
Liang et al.

(10) Patent No.: US 8,796,032 B2
(45) Date of Patent: Aug. 5, 2014

(54) METHOD FOR ANALYZING AND DETECTING CALCIUM ELEMENT IN ORE

(75) Inventors: Yulan Liang, Jiangxi (CN); Ling Peng, Jiangxi (CN); Zhijian Zhao, Jiangxi (CN)

(73) Assignee: Jiangxi Rare Earth and Rare Metals Tungsten Group Holding Co Ltd., Jiangxi (CN)

( * ) Notice: Subject to any disclaimer, the term of this patent is extended or adjusted under 35 U.S.C. 154(b) by 354 days.

(21) Appl. No.: 13/504,684

(22) PCT Filed: Dec. 30, 2009

(86) PCT No.: PCT/CN2009/076285
§ 371 (c)(1),
(2), (4) Date: Jun. 18, 2012

(87) PCT Pub. No.: WO2011/050552
PCT Pub. Date: May 5, 2011

(65) Prior Publication Data
US 2012/0252126 A1 Oct. 4, 2012

(30) Foreign Application Priority Data
Oct. 29, 2009 (CN) .......................... 2009 1 0236483

(51) Int. Cl.
*G01N 33/24* (2006.01)
*G01N 33/20* (2006.01)
*G01N 21/79* (2006.01)
*G01N 31/16* (2006.01)

(52) U.S. Cl.
CPC ................ *G01N 21/79* (2013.01); *G01N 33/24* (2013.01); *G01N 31/16* (2013.01)

USPC ................................................ 436/79; 436/26

(58) Field of Classification Search
USPC ..................................................... 436/26, 79
See application file for complete search history.

(56) References Cited

U.S. PATENT DOCUMENTS

| | | | | | |
|---|---|---|---|---|---|
| 3,159,586 A | * | 12/1964 | Wildenhayn | .................... | 436/79 |
| 3,709,662 A | * | 1/1973 | Hach | ............................... | 436/84 |
| 5,411,889 A | * | 5/1995 | Hoots et al. | ....................... | 436/6 |

FOREIGN PATENT DOCUMENTS

| | | | |
|---|---|---|---|
| CN | 101344489 A | | 1/2009 |
| GB | 922268 | * | 3/1963 |
| KR | 20070073682 A | | 7/2007 |
| RU | 2076322 C1 | | 3/1997 |

OTHER PUBLICATIONS van der Reyden, A. J. et al, Fresenius' Zeitschrift für Analytische Chemie 1962, 187, 241-250.*
Graham, Jr., H. G. et al, Journal of Agricultrual and Food Chemistry 1962, 10, 447-450.*

* cited by examiner

*Primary Examiner* — Arlen Soderquist
(74) *Attorney, Agent, or Firm* — Hammer & Associates, P.C.

(57) ABSTRACT

A method for determining the content of calcium element in an ore is provided. It includes: decomposing the ore with hydrochloric acid and nitric acid under heating condition, adding perchloric acid, cooling, adding a small amount of water and boiling the solution to dissolve the salts, then cooling, diluting to the constant volume, filtering into a dry beaker with dry filter-paper, masking interfering ions with triethanolamine, adjusting the pH value of the solution with KOH, using calcein-thymolphthalein as indicator, and determinating the content of calcium with EDTA titrimetry.

7 Claims, No Drawings

METHOD FOR ANALYZING AND DETECTING CALCIUM ELEMENT IN ORE

TECHNICAL FIELD

The present invention relates to a method for analyzing and detecting calcium element in an ore, particularly to a method for analytic determination of the calcium content in the ore.

PRIOR ART

Instrument analysis and conventional chemical analysis are mainly utilized for the determination of calcium content. While the instrumental analysis allows for an improved sensitivity of the analysis, carbonatite often contains a higher calcium content, thus the measurement error increases with a lower accuracy; the chemical analysis is mainly performed by EDTA complexometric titration and potassium permanganate volumetric method. Currently, the EDTA complexometric titration is commonly used for the determination of a normal calcium content, but one should select an appropriate indicator for particular ratio of the calcium ion content, and choose a suitable masking agent according to the contents of the interfering elements. The two chemical analysis methods require the addition of ammonium oxalate to precipitate calcium to separate from impurity elements, a long standing time for precipitation (more than two hours) is necessary, and multiple times of filtering and washing as well as a series of complex impurity separation procedures are needed, so that more reagents are required, with high cost, long process and low operating efficiency.

SUMMARY OF THE INVENTION

The object of this invention is to provide a simple, rapid and accurate method for analytic determination of the element content of calcium in an ore.

The technical solution of this invention is as follows: a sample is first decomposed by hydrochloric acid, nitric acid, and treated with perchloric acid till smoking; the above solution is then transferred to a volumetric flask and bring to constant volume, and filtered into a dry beaker through a dry filter-paper to remove impurity elements such as tungsten, molybdenum and the like; an appropriate amount of filtrate is taken, to which is added triethanolamine to mask interfering ions such as iron, manganese, aluminum and the like, and the pH value of which is adjusted with potassium hydroxide; calcein-thymolphthalein is added as a mixed indicator, and calcium is directly titrated with standard EDTA solution. Specific steps are as follows:

(1) Adding hydrochloric acid, nitric acid into a sample for heat treatment, adding perchloric acid till smoking, and after cooling, adding a small amount of water to dissolve the salts by boiling;

(2) After cooling the test solution, transferring it to an appropriate volumetric flask and bringing to constant volume, and filtering into a dry beaker through a dry filter-paper to separate calcium from tungsten, molybdenum and other impurity elements;

(3) Pipetting an appropriate amount of filtrate and adding triethanolamine to mask interfering ions;

(4) Adjusting the pH value of the solution with potassium hydroxide;

(5) Using calcein-thymolphthalein as a mixed indicator;

(6) Titrating directly for calcium content with standard EDTA solution and calculating for analysis results.

In said step (1), the hydrochloric acid used during heat treatment is a concentrated hydrochloric acid with a density of 1.19 g/mL, the nitric acid is a concentrated nitric acid with a density of 1.42 g/mL, and the perchloric acid is a concentrated acid with a density of 1.67 g/mL.

In said step (2), after the test solution is brought to constant volume, it is filtered into a dry beaker through a dry filter-paper, and the initial 5-10 mL filtrate is discarded.

In said step (3), the masking agent triethanolamine for masking interfering ions such as iron, aluminum, manganese and the like is a 30%-50% solution.

In said step (4), the pH value of the solution is adjusted with potassium hydroxide with a concentration of 100-200 g/L.

In said step (5), a mixed indicator calcein-thymolphthalein is used as the indicator.

In said step (6), the concentration of the standard EDTA solution for titration is 0.02-0.03 mol/L.

For the standard solutions required in the method of the invention, their preparation and calibration are as follows:

(1) Standard Calcium Solution

Accurately weighing 2.4972 g ovendried calcium carbonate (over 99.95%) and placing it in a 250 mL beaker, adding 10 mL hydrochloric acid solution (1+1) to dissolve it, followed by boiling for 1-2 min to remove carbon dioxide, cooling and transferring it to a 1000 mL volumetric flask, diluting with water to volume and shaking well. This solution contains 1.0 mg calcium per milliliter.

(2) Preparation and Calibration of the Standard EDTA Solution

Preparation: weighing 15-20 g $Na_2EDTA$ to dissolve in 200 mL hot water, filtering and cooling, then diluting to 2000 mL and mixing well, the concentration is 0.02-0.03 mol/L.

Calibration: pipetting 10.00 mL standard calcium solution (1.0 mg/mL) to a 250 mL beaker, diluting with water to 100 mL. The following steps are performed according to the present invention.

The titer of the standard EDTA solution for calcium is calculated as:

$$T = \frac{\rho \times V_3}{V_4}$$

where: T—titer of the standard EDTA solution for Ca (g/mL);
ρ—concentration of the standard calcium solution (g/mL);
$V_3$—volume of the standard calcium solution that is pipetted (mL);
$V_4$—volume of the standard EDTA solution consumed during calibration.

In the method of the invention, analysis results are calculated by titration methods as below:

$$Ca\% = \frac{T \times (V - V_0) \times V_1}{m \times V_2} \times 100$$

where: T—titer of the standard EDTA solution for Ca (g/mL);
V—volume of the standard EDTA solution consumed during titration (mL);
$V_0$—volume of the standard EDTA solution consumed during blank test (mL);
M—sample size (g);
$V_1$—total volume of the test solution (mL);
$V_2$—volume of the test solution taken (mL).

The present invention overcomes the shortcomings of conventional analytical methods for calcium, i.e. requiring multiple times of filtering and washing as well as a series of complex impurity separation procedure, requiring more reagents, high cost, long process and low operating efficiency; and provides a simple, rapid and accurate method for analytic determination of calcium content in an ore.

SPECIFIC EMBODIMENTS

In conjunction with the following example, the method for analyzing and detecting calcium element of the present invention is further illustrated in details.

EXAMPLE 1

Sample Determination (Sample A-0268, A-0269, WJ-101)

Weighing 0.2000-1.000 g sample into a 250 mL beaker, adding 10-15 mL hydrochloric acid with a density of 1.19 g/mL, covering with a watch glass, heating for 5-10 min to decompose, removing to cool down slightly, adding 5-10 mL nitric acid with a density of 1.42 g/mL, continuing heating to dissolve until about 3-5 mL solution is left, removing to cool down slightly, adding 1-4 mL perchloric acid with a density of 1.67 g/mL, heating till thickly smoking, removing to cool down, purging watch glass and beaker wall with water, heating to boil to dissolve the soluble salts, removing and cooling down to room temperature.

Transferring the above solution to an appropriate volumetric flask, bringing with water to volume and shaking well; filtering into a dry beaker through a dry filter-paper, discarding the initial 5-10 mL filtrate; taking an appropriate amount of filtrate from the original beaker, adding water to 100 mL, adding 20-30 mL triethanolamine solution with a concentration of 30%-50%, adjusting pH value of the solution with a potassium hydroxide solution with a concentration of 100-200 g/L, adding 0.1-0.2 g mixed indicator calcein-thymolphthalein, setting black as background and titrating with a standard EDTA solution with a concentration of 0.02-0.03 mol/L, with the disappearance of green fluorescence as end point. Blank tests were also performed.

Three samples were tested according to the method of the invention, each sample was tested for 6 times under identical conditions, analysis results were calculated according to the volume of the standard EDTA solution consumed and the titer of aforementioned standard EDTA solution for calcium, as shown in Table 1, test was also performed in accordance with Chinese Standard (GB/T6150.5-2008), and testing results were compared with those from Jiangxi Research Institute of Nonferrous metallurgy.

TABLE 1

Analysis results of calcium ω%

| Sample | Method of the invention | | | GB method | Jiangxi Research Institute of Nonferrous metallurgy |
|---|---|---|---|---|---|
| | measured value | average value | RSD | | |
| WJ-101 | 13.30, 13.38, 13.21, 13.39, 13.14, 13.16 | 13.26 | 0.83 | 13.10 | 13.30 |
| A-0268 | 1.23, 1.10, 1.19, 1.25, 1.21, 1.18 | 1.19 | 4.41 | 1.18 | 1.16 |
| A-0269 | 21.84, 21.91, 21.73, 21.79, 21.76, 22.01 | 21.84 | 0.48 | 21.63 | 21.87 |

The invention claimed is:

1. A method for analyzing and detecting calcium element in an ore, characterized by the following steps:
   (1) adding hydrochloric acid and nitric acid into a sample for heat treatment, adding perchloric acid till smoking, and after cooling, adding a small amount of water to dissolve the salts by boiling;
   (2) after cooling the test solution, transferring it to a 100-250 mL volumetric flask and bringing to volume, and filtering into a dry beaker through a dry filter-paper to separate calcium at least in part from impurity elements such as tungsten and molybdenum;
   (3) pipetting an appropriate amount of filtrate and adding triethanolamine to mask interfering ions;
   (4) adjusting the pH value of the solution with potassium hydroxide;
   (5) using calcein-thymolphthalein as a mixed indicator; and
   (6) titrating directly for calcium content with a standard EDTA solution and calculating for analysis results.

2. The method according to claim 1, characterized in that in step (1), the hydrochloric acid is a concentrated hydrochloric acid with a density of 1.19 g/mL, the nitric acid is a concentrated nitric acid with a density of 1.42 g/mL, and the perchloric acid is a concentrated acid with a density of 1.67 g/mL.

3. The method according to claim 1, characterized in that a part of impurity elements of tungsten and molybdenum are removed in step (2).

4. The method according to claim 1, characterized in that the concentration of triethanolamine solution in step (3) is 30%-50%.

5. The method according to claim 1, characterized in that in step (4), the pH value of the solution is adjusted with potassium hydroxide with a concentration of 100-200 g/L.

6. The method according to claim 1, characterized in that in step (5), calcein-thymolphthalein is used as a mixed indicator.

7. The method according to claim 1, characterized in that in step (6), the concentration of the standard EDTA solution for titrating calcium element is 0.02-0.03 mol/L.

* * * * *